US008483474B2

(12) United States Patent
Monfort

(10) Patent No.: US 8,483,474 B2
(45) Date of Patent: Jul. 9, 2013

(54) METHOD OF MEASURING THE CLEANNESS OF STEEL STRIP

(75) Inventor: Guy Monfort, Montegnée (BE)

(73) Assignee: Centre de Recherches Métallurgiques asbl—Centrum voor Research in de Metallurgie vzw, Brussels (BE)

( * ) Notice: Subject to any disclaimer, the term of this patent is extended or adjusted under 35 U.S.C. 154(b) by 432 days.

(21) Appl. No.: 12/736,767

(22) PCT Filed: Mar. 12, 2009

(86) PCT No.: PCT/EP2009/052926
§ 371 (c)(1),
(2), (4) Date: Nov. 8, 2010

(87) PCT Pub. No.: WO2009/138262
PCT Pub. Date: Nov. 19, 2009

(65) Prior Publication Data
US 2011/0051994 A1 Mar. 3, 2011

(30) Foreign Application Priority Data
May 14, 2008 (BE) .................................. 2008/0270

(51) Int. Cl.
*G06K 9/00* (2006.01)
*G01N 21/71* (2006.01)
*G01N 21/67* (2006.01)
*G06T 7/00* (2006.01)

(52) U.S. Cl.
CPC .............. *G01N 21/718* (2013.01); *G01N 21/67* (2013.01); *G06T 7/0004* (2013.01)

USPC ........................................... 382/141; 382/168

(58) Field of Classification Search
None
See application file for complete search history.

(56) References Cited

U.S. PATENT DOCUMENTS
6,795,179 B2 * 9/2004 Kumar .......................... 356/318

FOREIGN PATENT DOCUMENTS
JP   05-172762   7/1993
JP   2002-195950   7/2002

OTHER PUBLICATIONS

Balzer et al. (2005) "Online coating thickness measurement and depth profiling of zinc coated sheet steel by laser induced breakdown spectroscopy." Spectrochimica Acta Part B vol. 60, pp. 1172-1178.*
Mateo et al. (2003) "Automated line-focused laser ablation for mapping of inclusions in stainless steel." Applied Spectroscopy, vol. 57 No. 12, pp. 1461-1467.*

(Continued)

*Primary Examiner* — Barry Drennan
(74) *Attorney, Agent, or Firm* — Jacobson Holman PLLC

(57) ABSTRACT

The present invention relates to an automated in-line method for measuring the surface cleanness of a continuously running metal sheet or strip, characterized by the following steps: a beam of radiation or a particle beam or a spark is focused onto the surface of the running strip, the transmitted power and the focal diameter being chosen so as to obtain a power density sufficient to create a plasma or hot spot which locally etches the metal in the form of a central zone surrounded by a peripheral oxidation ring; the characteristics of a zone encompassing said oxidized ring and possibly said central zone are analyzed by means of an optical image acquisition device and image processing; and an objective value indicative of the surface cleanness is deduced therefrom.

9 Claims, 2 Drawing Sheets

OTHER PUBLICATIONS

Orzi et al. (2004) "Identification and measurement of dirt composition of manufactured steel plates using laser-induced breakdown spectroscopy." Applied Spectroscopy, vol. 58 No. 12, pp. 1475-1480.*

Zhang et al. (2002) "Evaluation and control of steel cleanliness—Review." Proc. 85$^{th}$ ISS-AIME Steelmaking Conf., pp. 431-452.*

P.J. Krauth, "Contrôle de la propreté des surfaces d'aciers," La Revue de Métallurgie, 2002, pp. 561-568 (Partial English translation).

G.M. Bilmes et al., "A real time method for surface cleanliness measurement," Applied Physics B: Lasers and Optics, 2006, vol. 82, No. 4, pp. 643-648.

Innsitec Laser Technologies GmbH, CoilScooter-TG, Transportable LIBS system for remote chemical elemental analysis—TeleLis, http://www.innsitec.com, (Jun. 2005).

* cited by examiner

METHOD OF MEASURING THE CLEANNESS OF STEEL STRIP

This is a national stage of PCT/EP09/052926 filed Mar. 12, 2009 and published in French, which has a priority of Belgium no. BE2008/0270 filed May 14, 2008, hereby incorporated by reference.

FIELD OF THE INVENTION

The present invention relates to an in-line method for measuring the surface cleanliness of steel sheets or strips.

TECHNOLOGICAL BACKGROUND OF THE INVENTION AND PRIOR ART

During the manufacture of steel sheets, the cold rolling process essentially creates two types of impurities on the sheet surface: first, surface carbon, which comes from the degradation of the rolling oils, and secondly, iron fines from the interactions with the cylinders used for rolling.

This surface pollution is problematic because it requires more frequent cleaning of the cylinders and the pickling baths are more quickly polluted. This obviously entails additional costs. The dirty sheets also have to be annealed longer, which is also more costly. Lastly, in the subsequent galvanization or painting steps, these depositions amount to adhesion flaws that have consequences on the corrosion resistance of the finished products.

To assess the surface cleanliness, there are two different methods that can be classified in two groups:
- laboratory methods, which are precise but "off-line." These methods are based on X-ray fluorescence, atomic absorption, mass spectrometry, etc. They generally require a long time and are costly to implement;
- in-line control methods, which are generally quick but less precise. Among those, the "Scotch® Tape Test" (or Tesa-Test) is the best known method. It consists in applying on the sheet, in the most reproducible manner possible, a piece of adhesive, hereinafter called "Scotch® tape", that will then be removed and stuck on white paper. The percentage of light reflected by the "Scotch® tape" charged with particles removed from the sheet is then measured. This is done either by comparison with standards, or using a specific device.

This last method however depends on the operator, and in particular on the way that the Scotch® tape is applied on the sheet (application speed, pressure, removal speed, etc.). It results in a significant dispersion of the results, which can reach more than 20% on the reflectivity measurement.

Recently, a semi-automatic method was developed. This method allows to automatically apply the "Scotch® tape" on the sheet, which may be in motion, then to measure the reflectivity percentage, also done automatically. However, an operator is still present and the dispersion of the results is apparently only barely lower. Furthermore, the discontinuous nature of the measurements remains a major drawback (cf. CoilScooter-TG apparatus by the company INNSITEC Laser technologies GmbH—www.innsitec.com).

Even more recently, a completely automatic method based on the absorption of infrared radiation was studied. To our knowledge, it is still being developed and, in any case, is not widely spread (see Krauth P. J., "Contrôle de la propreté des surfaces d'acier", La Revue de Métallurgie—CIT, June 2002).

AIMS OF THE INVENTION

The present invention aims to provide an in-line and continuous method for measuring the surface cleanliness of steel strips, which allows to overcome the drawbacks of the prior art.

The invention more particularly aims to provide a reliable, reproducible and completely automated method.

MAIN CHARACTERISTIC ELEMENTS OF THE INVENTION

The present invention relates to an in-line and automated method for measuring the surface cleanliness of a metal sheet or strip in continuous motion, wherein:
- a beam of radiation or of particles or even a spark is focused onto the surface of the strip in motion, the transmitted power and the focal diameter being chosen so as to obtain sufficient power density to create a plasma or hot spot which locally etches the metal in the form of a central zone surrounded by a peripheral oxidation ring;
- the characteristics of a zone encompassing said oxidized ring and possibly said central zone are analyzed by means of an optical image-acquisition device and by image processing;
- an objective value indicative of the surface cleanliness is deduced therefrom.

Preferred embodiments of the invention also disclose one or several of the following features in combination:
- said beam is a laser beam or an electron beam;
- the optical image-acquisition device is a camera that is active in the ultraviolet, visible and/or infrared region;
- the image processing comprises an analysis of the width of the oxidation ring and/or of the intensity of its coloration;
- acquired color images are converted into gray scale and their corrected histograms are established;
- the brightness is adapted in the image processing so that the average values of the histograms corresponding to a clean standard sheet and a dirty standard sheet, respectively, may be compared;
- for each sheet to be examined, a zone encompassing said central zone surrounded by a peripheral oxidation ring is defined and the average value or the median of the histogram corresponding to that zone is calculated, the cleanliness of the sheet being deemed satisfactory for an average or median value greater than a value predetermined by calibration on a clean sheet and a dirty sheet;
- the metal strip or sheet is made of steel;
- the motion speed of the metal strip or sheet is greater than 0.5 m/s.

SHORT DESCRIPTION OF THE FIGURES

Figure 3:
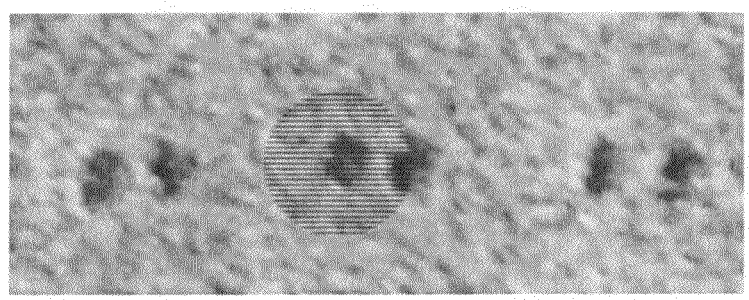

In FIG. 3, the hatched zone indicates the zone used to define the local histogram, whose average value allows to quantify the cleanliness level (clean sheet).

Figure 4:
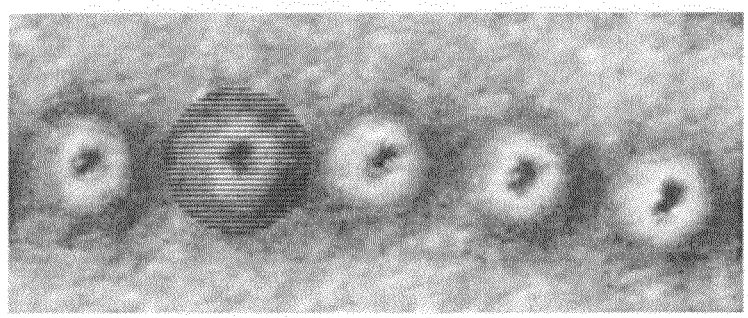

In FIG. 4, the hatched zone indicates the zone used to define the local histogram, whose average value allows to quantify the cleanliness level (dirty sheet).

Figure 5:
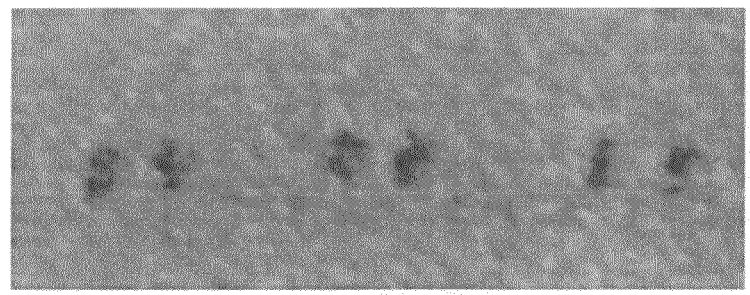

FIG. 5 is the start photograph of the clean sheet.

Figure 6:
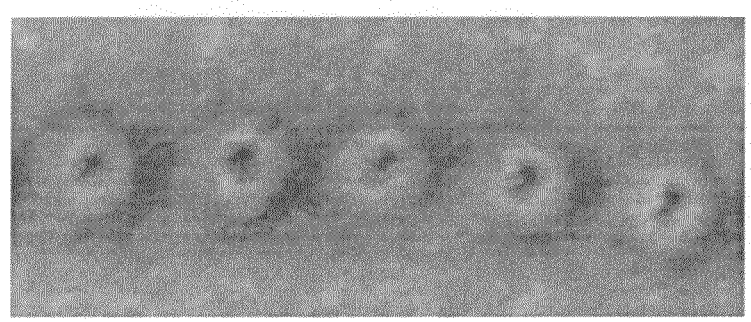

FIG. 6 is the start photograph of the dirty sheet.

DESCRIPTION OF A PREFERRED EMBODIMENT OF THE INVENTION

The device proposed in the invention belongs to the category of fully-automated measuring devices. It may be placed on an industrial line and operate without operator intervention.

The principle of the device is described below.

A laser beam, preferably pulsed, is focused on the surface of the sheet in motion. The laser power and focal diameter are chosen such that the power density obtained on the sheet is sufficient to create a plasma on the surface of the sheet.

Under these conditions, one notes the formation of an oxidation ring surrounding the plasma zone. This ring has a width and a brownish color that depend on the surface cleanliness.

By analyzing the characteristics of the oxidation zone with a camera or any other equivalent device, it is possible to deduce a value indicative of the surface cleanliness independent from an operator's subjectivity.

Processing of the image consists in analyzing the width of the affected zone and/or the intensity of its coloring.

Example of Application of the Method

In the following example, the laser source used is that included in the TeleLis, LIBS laser apparatus by the firm LSA—Laser Analytical Systems & Automation GmbH, Aachen.

The laser beam, with an energy of 300 mJ, is focused 150 mm under the surface of the sheet to be measured, the source being situated 4 meters from the sheet. The sheet moves at a linear velocity of about 0.6 m/s. The laser operates in "double-pulse" mode with a repetition frequency of 20 Hz.

With each pulse, a plasma is generated and a micro-crater is created on the surface of the sheet. Its depth depends on the energy of the laser. Around the crater, a more or less dark brownish zone appears: surprisingly, it has been noted that the intensity of its color and its width depend on the surface cleanliness of the sheet.

Figure 1:
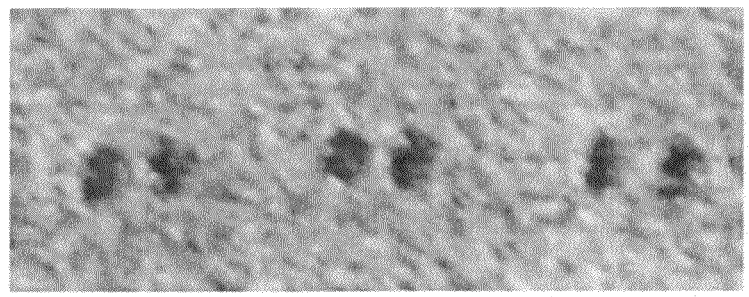
FIG. 1 shows a view of six laser craters on a clean sheet, after the color image is converted into gray scale and the histogram is corrected according to the method of the present invention.
Figure 2:
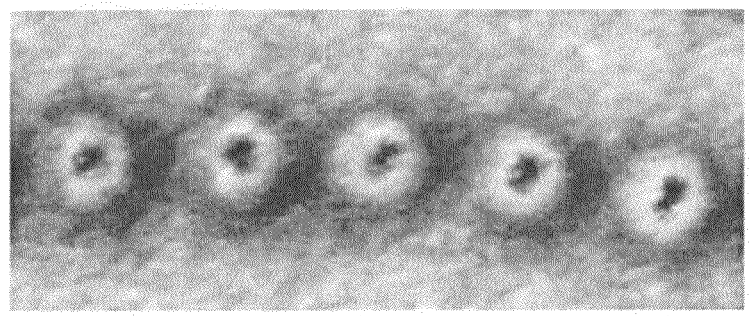
FIG. 2 shows a view of five laser craters on a dirty sheet, after the color image is converted into gray scale and the histogram is corrected according to the method of the present invention.

As an example, FIGS. 1 and 2 show images of some craters obtained for a clean sheet and for a dirty sheet, respectively. These images, which have similar magnifications, were converted into gray scale from color photographs and the brightness was adapted so that the two photos have a comparable average value of their histograms. In the illustrated example, this value is 129.

It is therefore noted that, for the dirty sheet, a dark ring is clearly visible around each crater, the central point being black, whereas it almost does not appear at all for the clean sheet.

If, in both cases, a well-defined zone is delimited around a crater (hatched zone in FIGS. 3 and 4) and the *average values of the histograms for those zones are then used, a value of 100 for the dirty sheet and of 120 for the clean sheet is obtained, respectively.

The difference is even more pronounced if the median, which is 88 and 131, respectively, is used. In comparison, the traditional reflectivity measurements used to determine surface cleanliness yield values of about 58% and 38%, respectively. It will be noted that the reflectivity percentage values decrease the dirtier the sheet is, whereas the average value of the local histogram increases.

These criteria based on the histogram are only one of the possibilities for quantifying the cleanliness of the sheets based on an automatic image analysis. More sophisticated processing known by those skilled in the art would allow even deeper discrimination. Indeed, weak coloring of the ring is visible to the naked eye for the clean sheet, whereas the basic gray-scale conversion applied as above makes it disappear completely, thus reducing the discriminating power of the method.

For information, FIGS. 5 and 6 show start color photos.

Advantages Of The Method

This method has the advantage of being completely automated and therefore does not depend on the dexterity and judgment of an operator.

It may also work on a sheet in motion for continuous monitoring.

Lastly, it only requires simple and robust material, that may be used on industrial lines, at a sufficient distance to avoid damage in case of an incident.

The invention claimed is:

1. An in-line, automated method for measuring the surface cleanliness of a metal sheet or strip in continuous motion, comprising:
    focusing a beam of radiation or of particles onto the surface of the sheet or strip in motion, the transmitted power and the focal diameter of the beam being chosen so as to obtain sufficient power density to create a plasma or hot spot which locally etches the metal in the form of a central zone surrounded by a peripheral oxidation ring;
    analyzing the characteristics of a zone encompassing said oxidation ring by means of an optical image-acquisition device and by image processing;
    deducing an objective value indicative of the surface cleanliness from said analysis.

2. The method as in claim 1, wherein said beam is a laser beam or an electron beam.

3. The method as in claim 1, wherein the optical image-acquisition device is a camera that is active in the ultraviolet, visible and/or infrared region.

4. The method as in claim 1, wherein the image processing comprises analyzing the width and/or the coloration of the oxidation ring.

5. The method as in claim 1, further comprising acquiring color images using the optical image-acquisition device, wherein the image processing comprises converting the acquired color images into gray scale and establishing corrected histograms of the converted images.

6. The method as in claim 5, wherein the image processing further comprises adapting the brightness of the converted images so that the average values of said histograms may be compared to the average values of histograms corresponding to a clean standard sheet and to a dirty standard sheet.

7. The method as in claim 6, wherein the image processing further comprises:
    for each sheet to be examined, defining a zone encompassing said central zone surrounded by a peripheral oxidation ring,
    calculating the average value or the median of the histogram corresponding to that zone, and
    deeming the cleanliness of the sheet satisfactory for an average or median value greater than a value predetermined by calibration on a clean sheet and on a dirty sheet.

8. The method according to claim 1, wherein the metal strip or sheet is made of steel.

9. The method according to claim 1, wherein the motion speed of the metal strip or sheet is greater than 0.5 m/s.

* * * * *